(12) United States Patent
Berbers

(10) Patent No.: US 8,696,615 B2
(45) Date of Patent: Apr. 15, 2014

(54) ARRANGEMENT FOR TRANSFERRING AN OVUM FROM A FOLLICLE

(75) Inventor: Josephus E. J. M. Berbers, Malden (NL)

(73) Assignee: Gynotec, Malden (NL)

( * ) Notice: Subject to any disclaimer, the term of this patent is extended or adjusted under 35 U.S.C. 154(b) by 806 days.

(21) Appl. No.: 12/604,637

(22) Filed: Oct. 23, 2009

(65) Prior Publication Data

US 2010/0081989 A1 Apr. 1, 2010

Related U.S. Application Data

(63) Continuation-in-part of application No. PCT/NL2008/050224, filed on Apr. 18, 2008.

(30) Foreign Application Priority Data

Apr. 24, 2007 (NL) ...................................... 2000606

(51) Int. Cl.
*A61M 3/00* (2006.01)

(52) U.S. Cl.
USPC .................. 604/44; 604/27; 604/28; 604/35; 604/43; 604/515

(58) Field of Classification Search
USPC ............... 604/27, 35, 44, 158, 173, 264, 272, 604/533–535, 43, 515, 28; 600/33–35
See application file for complete search history.

(56) References Cited

U.S. PATENT DOCUMENTS

| 4,055,187 | A | * | 10/1977 | Patel et al. | 604/103 |
| 4,601,713 | A | * | 7/1986 | Fuqua | 604/514 |
| 5,160,319 | A | * | 11/1992 | Emery et al. | 604/27 |

(Continued)

FOREIGN PATENT DOCUMENTS

| DE | 3522782 | 1/1987 |
| DE | 3702441 | 8/1988 |
| EP | 1158913 | 12/2001 |

(Continued)

*Primary Examiner* — Bhisma Mehta
*Assistant Examiner* — Larry R Wilson
(74) *Attorney, Agent, or Firm* — Jeffrey D. Myers; Peacock Myers, P.C.

(57) ABSTRACT

An apparatus for transferring an ovum from a follicle with a double lumen needle having at the distal needle end an aspiration lumen for removing an ovum from a follicle and a flushing lumen, the double lumen needle including an outer tube with an internally located inner tube that extends over at least part of the length of the outer tube, one of the lumens being bounded by the inner surface of the inner tube and the other of the two lumens by the space between the outer surface of the inner tube and the inner surface of the outer tube, and a connector having an outlet at a second connector end for discharging the flushing fluid with possibly an ovum to the exterior and having a channel that connects the outlet with the aspiration lumen and a flushing inlet for supplying the flushing fluid, such that the two fluid pathways within the connector and the double lumen needle are separated from each other, and the inner tube comprises a deformable material. The lumen of the inner tube is the aspiration lumen and the inner tube comprises a depressible portion that is depressible under the influence of a pressure difference between the aspiration lumen and the flushing lumen and the flushing lumen is the space between the interior surface of the outer tube and the exterior surface of the depressible portion.

13 Claims, 4 Drawing Sheets

(56) References Cited

U.S. PATENT DOCUMENTS

| | | | |
|---|---|---|---|
| 5,643,309 A * | 7/1997 | Myler et al. | 623/1.15 |
| 5,700,251 A * | 12/1997 | Miyauchi et al. | 604/264 |
| 5,792,300 A * | 8/1998 | Inderbitzen et al. | 156/244.13 |
| 6,607,503 B1 | 8/2003 | Berbers | |
| 6,706,055 B2 * | 3/2004 | Douk et al. | 606/200 |
| 7,455,806 B2 * | 11/2008 | Junger et al. | 264/516 |

FOREIGN PATENT DOCUMENTS

| | | | | |
|---|---|---|---|---|
| WO | WO 86/06968 | 12/1986 | | |
| WO | WO 00/53108 | 9/2000 | | |
| WO | WO 0053108 A1 * | 9/2000 | | A61B 17/435 |

* cited by examiner

US 8,696,615 B2

ARRANGEMENT FOR TRANSFERRING AN OVUM FROM A FOLLICLE

This application is a continuation-in-part application of International Patent Application Serial No. PCT/NL2008/050224, entitled "Arrangement for Transferring an Ovum from a Follicle", by Josephus Elbertus Johanna Maria Berbers, to GYNOTEC, filed on Apr. 18, 2008, and the specification and claims thereof are incorporated herein by reference.

This application claims priority to and the benefit of the filing of Netherlands Patent Application Serial No. 2000606, entitled "Arrangement for Transferring an Ovum from a Follicle", filed on Apr. 24, 2007, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to an apparatus for transferring an ovum from a follicle with a combined technique of flushing and aspiration, which apparatus comprises:
  a double lumen needle having at the distal needle end to be inserted into the follicle an aspiration lumen for removing an ovum from a follicle and a flushing lumen for inserting a flushing fluid into the follicle, the double lumen needle comprising an outer tube with an internally located inner tube that extends over at least part of the length of the outer tube, one of the lumens being bounded by the inner surface of the inner tube and the other of the two lumens by the space between the outer surface of the inner tube and the inner surface of the outer tube, and
  a connector having a connector body which at a first distal connector end is connected to the proximal needle end remote from the distal needle end, having an outlet at a second connector end for discharging the flushing fluid with possibly an ovum to the exterior and having a channel means that connects the outlet with the aspiration lumen and defines a first fluid pathway for aspirating an ovum and having a flushing inlet between the two ends of the connector body for supplying the flushing fluid and, in fluid communication with the flushing lumen, for defining a second fluid pathway for flushing a follicle,
  wherein the two fluid pathways within the connector and the double lumen needle are separated from each other, and
  wherein the inner tube comprises a deformable material.

2. Description of Related Art

An apparatus of the above-mentioned type is known from the European patent EP 1 158 913. With this Known apparatus the diameters of the inner tube are considerably smaller than the inside diameter of the outer tube. The inner tube is comprised of a flexible material, the flushing lumen is bounded by the interior wall of the outer tube and the aspiration lumen is bounded by the space between the exterior wall of the inner tube and the interior wall of the outer tube. An important drawback of this apparatus is the problem of leading the inner tube out of the outer tube. At the proximal end of the double lumen needle a connector is provided around the needle, within which connector the inner tube is brought into fluid communication with an external source for supplying flushing fluid. The inner tube should be readily deformable and is made of a thin flexible material. A first problem is that the delicate flexible tube has to be fed through an opening in the wall of the outer tube. There is a chance of the inner tube becoming damaged. It should be borne in mind that the outer diameter of the double lumen needle is approximately 1.6 mm. Thus the opening through the wall of the outer tube for feeding through the inner tube is correspondingly smaller. Moreover, connecting the flexible inner tube, for example, to a feed tube for flushing fluid and injecting the coupling to form an injection moulded connector is not simple, and may easily result in damage and production failure. Another problem in this known apparatus is fixing the inner tube to the interior wall of the outer tube. The use of adhesive in the production is problematic and less suitable for the purpose of the apparatus, i.e. transferring an ovum from a follicle. Adhesive contains chemical substances which are best avoided in such an environment.

It is an object of the invention to provide an apparatus of the kind mentioned in the preamble, wherein these problems are solved and which also encompasses other advantages. To realize this objective, the invention of the kind mentioned in the preamble is achieved by the measures mentioned in the characterizing part of claim 1.

In the apparatus for transferring an ovum from a follicle in accordance with the invention, the aspiration lumen is located completely at the inside of the inner tube. Due to the pressure difference prevailing between the flushing fluid in the flushing lumen and the interior of the aspiration lumen caused by flushing fluid that is being fed between the outer surface of the inner tube and the inner surface of the outer tube, the inner tube can over at least part of its circumference be depressed from the outside inward. The inner tube must now of course have a diameter large enough to allow an ovum to pass through. Due to the fact that here the inner tube has a much larger diameter than the inner tube of the above-mentioned EP 1 158 913, the possibilities to fix the inner tube to the interior wall of the outer tube are much better because the available surface is much larger. A further advantage is that the ovum, with tissue from the follicle possibly surrounding it, is only in contact with one material, namely the material of the inner tube.

The document WO 86/06968 relates to an apparatus for transferring an ovum from a follicle, comprising a needle with a larger diameter having a single lumen operating as aspiration lumen and, provided on the outside thereof, a tube with a smaller diameter and provided with a flushing lumen. As the outer tube is located at the outside, the cross section of the apparatus is not round, which is a drawback because after introduction into a patient, the apparatus must be easily rotatable about its axis without causing injury.

From DE 35 22 782 a double lumen needle is known, comprising an outer tube made of metal and fitting into this an inner tube made of metal, which is indented over part of its circumference so as to form a flushing lumen between the outer tube and the inner tube. Thus the inner tube is the aspiration tube, so that in this known apparatus also the follicle and the tissue possibly surrounding it come into contact only with the material of the aspiration tube. The manufacture of this type of apparatus is costly because the inner tube must be fabricated with precision so as to fit into the outer tube and in order to provide the depression on the inner tube, the outside of the thin metal inner tube has to undergo an difficult treatment. Providing a depression of, for example, 0.3 mm in a metal tube with a diameter of 1.26 mm requires an extra processing step which is not simple in itself.

Aü-B-68184/87 also relates to an apparatus for transferring an ovum from a follicle, provided with a double lumen needle. The inner tube of this apparatus is also made of metal and provided with a depression on the circumference so as to provide a flushing lumen between the interior wall of the outer tube and the exterior wall of the inner tube. This known apparatus has the same drawbacks as those mentioned in the discussion of DE 25 22 782.

For so far they are relevant, the contents of the above-mentioned prior art documents are herewith imported by-reference in the present specification.

SUMMARY DESCRIPTION OF THE INVENTION

Below a number of preferred embodiments of the invention will be discussed in concurrence with the appended sub-claims.

Because the space within the outer tube is utilized optimally, an apparatus in accordance with claim 2 of the invention is obtained that has a small diameter. The outside diameter of the outer tube may be in the order of, for example, 1.6 mm and the inside diameter in the order of, for example, 1.3 mm.

In the embodiment according to claim 3, the inner tube has a variable wall thickness where, viewed cross sectionally, a thicker portion is followed by a thinner portion. The depressible part is at the thinner portion, so that the remaining part of the inner tube may be more robust. If desired, the embodiment of claim 4 may be used by manufacturing the depressible part of the inner tube in a different material than the remaining part of the inner tube. For example, it is possible to use a more flexible material.

According to claim 5, it is ensured that, irrespective of which material the inner tube is made, at least its inner surface which comes in contact with a follicle and the tissue possibly surrounding it, is made of a biocompatible material. According to claim 6, the entire inner tube is made of a biocompatible plastic. The person skilled in the art of the respective field of medical applications is acquainted with sundry biocompatible plastics.

Claim 7 relates to a convenient method of manufacturing an inner tube in two different plastic materials. The technique of co-extrusion is well advanced in the art and it directly available for the application currently intended.

An important embodiment is that according to claim 8, wherein the depressible part of the inner tube is visibly distinguished from the remaining part, for example, through the colour and/or a surface structure and/or the degree of opacity of the material. It is of importance that during assembly of the apparatus according to the invention, the depressible part of the inner tube is placed correctly in relation to the position of the sharp point of the outer tube and in relation to the feed channel for the flushing fluid for the flushing lumen. As the depressible part in this embodiment of the invention is visibly distinguishable from the remaining part of the inner tube, an assembly in the correct position is easily realized.

It is preferred to use the embodiment of claim 1. Here the entire inner tube is made of elastic material and the depressible part is elastically deformable. In principle it is, of course, also possible to make the depressible part not or not completely elastic, but this could form an obstruction for an ovum possibly surrounded by tissue, moving through the inner tube.

Also interesting is an embodiment of the invention in accordance with claim 1. This embodiment comprises an inner tube made entirely of elastic material, which after assembly exerts a radial pressure against the outer tube. The choice of material of the inner tube, its wall thicknesses, the dimensions prior to axial stretching as well as in the stretched condition, and the inside diameter of the outer tube may be adjusted to each other such that after assembly of the inner tube in the outer tube, the inner tube exerts an elastic radial pressure on the interior surface of the outer tube. This pressure may be of sufficient force to generate so much friction between the interior wall of the outer tube and the exterior wall of the inner tube that without further means for attaching the inner tube to the outer tube, the inner tube remains in place in all situations occurring in practice. Thus an apparatus for the removal of an ovum from a follicle in accordance with the invention is provided, that can be manufactured at low costs of which neither the diameters of the outer tube nor those of the inner tube need to be critical.

Of importance is also a method according to the invention as described in claim 9. This method is used for the manufacture of the apparatus in accordance with claim 1 discussed above. In this embodiment it would be easy, for example with the aid of a wire of a tie rod or the like, to pass the axially stretched inner tube through the outer tube. After cancelling the tensile forces exerted on the inner tube, the radial elastic expansion causes the inner tube to jam against the interior wall of the outer tube and, if desired, may be suitably cut to length. Thus the inner tube may consist of, for example, a piece of a tubular elastic material that is rolled off a coil. By implementing claim 8 it is easy to ensure that the inner tube is positioned correctly before cancelling the tensile forces and the inner tube is positioned against the interior wall of the outer tube.

Of importance is further the embodiment of the apparatus in accordance with claim 10. In this embodiment, the connector can be easily manufactured by injection moulding and applied, with the outer tube being connected in a very simple manner by way of an outwardly fluid proof connection with a feed channel for flushing fluid.

Claim 11 describes an embodiment wherein the channel means connecting the outlet of the apparatus with the aspiration lumen of the double lumen needle is comprised of a flexible aspiration tube made, for example, of HDPE (high-density polyethylene).

The connection can be manufactured quickly and simply, for example, as described in claim 12.

Claim 13 finally describes a fast and economical manner of forming a flushing inlet inside the connector.

BRIEF DESCRIPTION OF THE SEVERAL VIEWS OF THE DRAWINGS

The invention will now be further explained with reference to the drawing, which exclusively by way of a non-limiting example shows a number of embodiments of the invention, and wherein.

Figure 1:
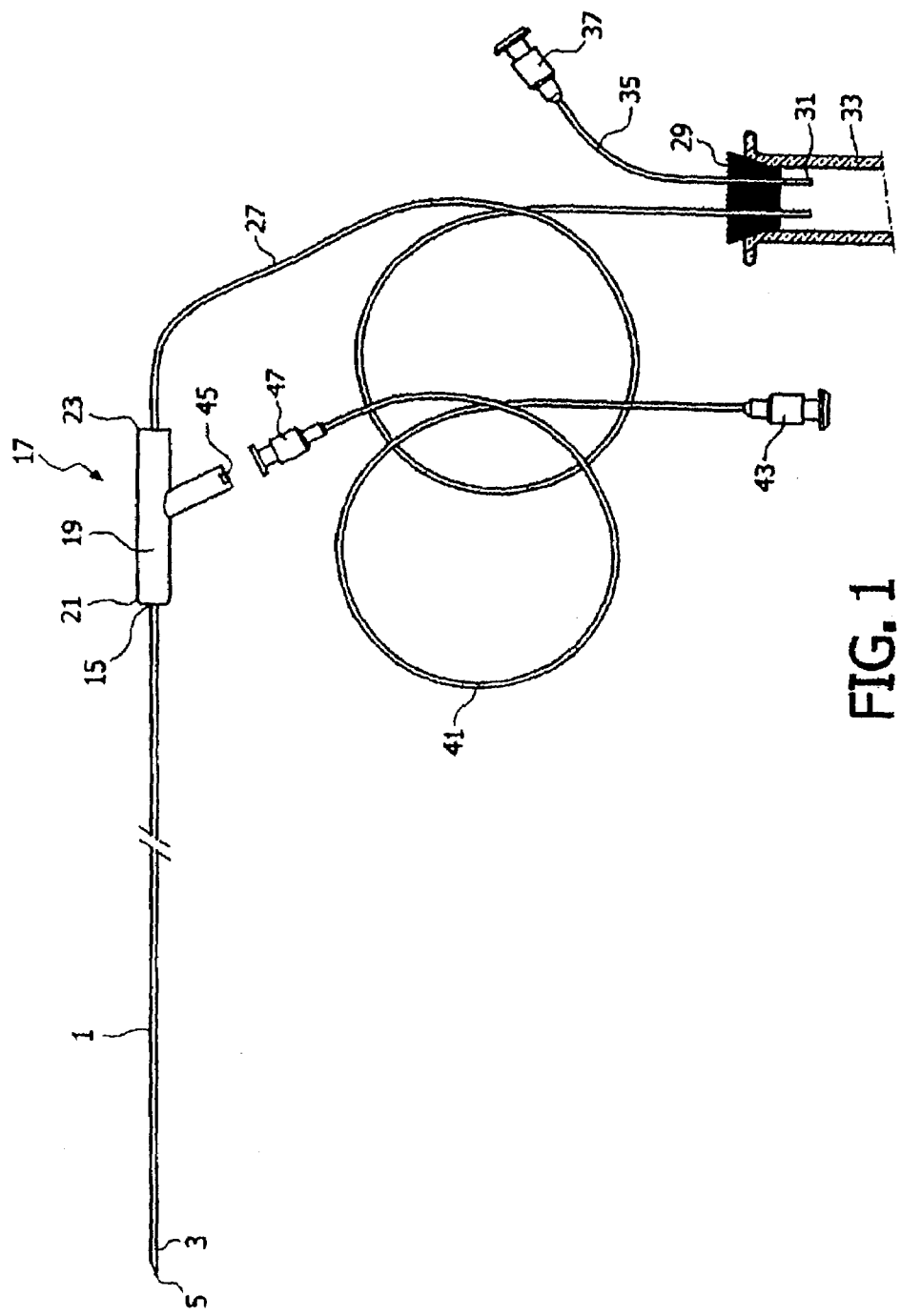
FIG. 1 shows a general side view of an apparatus according to the invention, comprising a double lumen needle, a connector and tubes to be connected to the connector for the supply of flushing fluid and for discharging an ovum to the exterior.

Similar elements in the various Figures are denoted by similar reference characters. Attention is drawn to the fact that in the Figures no attempt has been made to represent the various elements on the same or even the true scale. In this respect the Figures are merely intended for explanatory purposes and neither the measurements nor the proportions need to be consistent with reality. The term "distal" in the foregoing and in the description hereinafter, relates to a position that is further removed from a person operating the apparatus according to the invention than a position closer to the person. In contrast, the term "proximal" relates to a position that is closer to the said person than a position that is further removed.

DETAILED DESCRIPTION OF THE INVENTION

Figure 3:
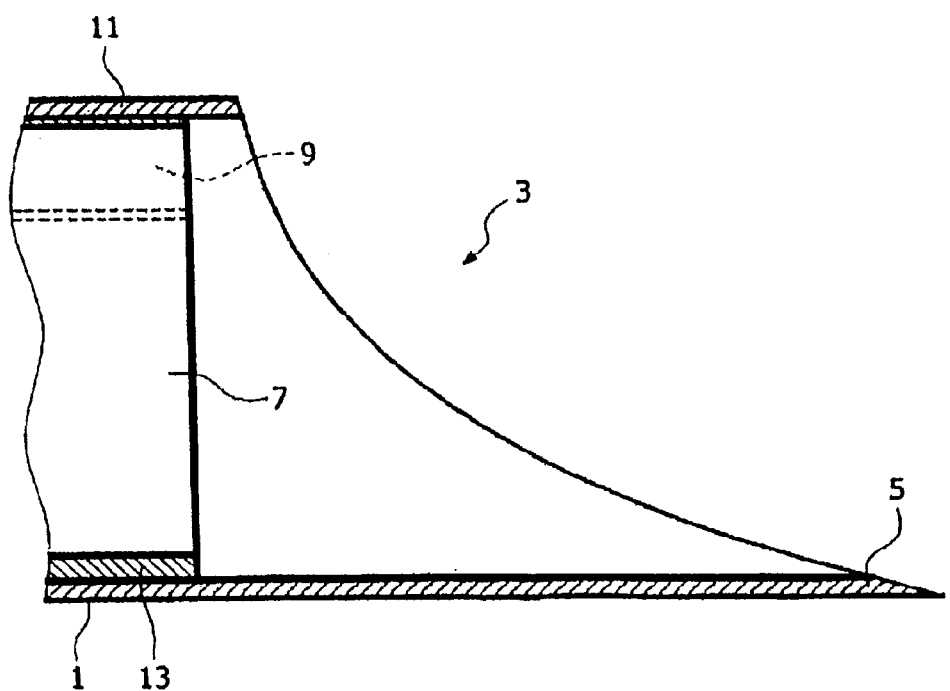
FIG. 3 shows an example of the sharp end of a double lumen needle having a cross section in accordance with FIG. 2.

The apparatus of FIG. 1 is provided with a double lumen needle having an elongate needle body 1. As can be clearly seen in FIGS. 1 and 3, there is a sharp point 5 at the distal needle end 3 to be inserted into the follicle, because the distal end is locally honed to taper and, as shown in particular in FIG. 3, it is slightly concave. Near the end 3 of the needle there is an aspiration lumen 7 present inside the double lumen needle 1, for removing an ovum from a follicle, not shown in the drawing, and a flushing lumen 9 for introducing a flushing fluid into the follicle. The double lumen needle 1 comprises an outer tube 11 and an inner tube 13, which extends at least over part of the length of the outer tube 11. As shown in FIG. 3, the inner tube 13 stops just short of the sharp point 5 provided at the outer tube. However, the inner tube may also extend more towards the point 5 and its distal end may, during honing of the sharp point, receive a corresponding form.

Figure 5:
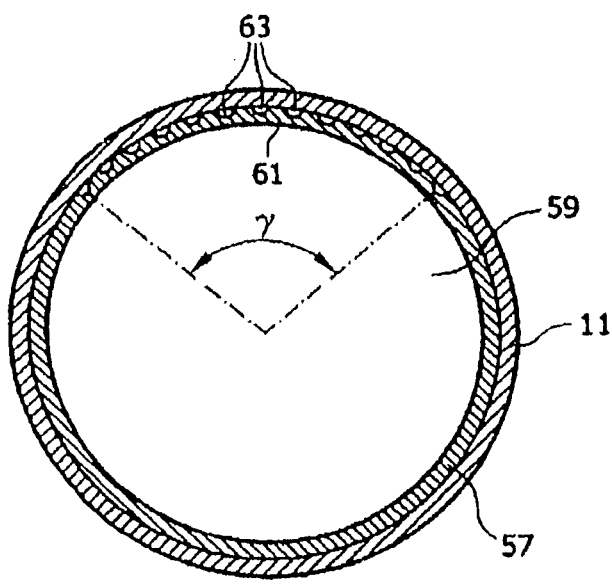
FIG. 5 shows a cross section similar to that of FIG. 2 and FIG. 4 of still another embodiment.

At the side 15 facing away from the distal end 3, the double lumen needle 1 is in communication with an injection-moulded connector 17, see FIGS. 1 and 5. The connector 17 comprises a connector body 19, which at a distal end 21 is in communication with the needle end 15 of the double lumen needle 1 that faces away from the distal needle end 3. At a proximal end 23, the connector 19 is provided with an outlet 25 for discharging an ovum. To this end the connector 17 is connected to an aspiration tube 27 made of a suitable plastic material such as HDPE (high-density polyethylene).

At the end facing away from the connector 17, the aspiration tube 27 is received in a stopper 29 made of a suitable elastic material, such as silicon rubber, through which the aspiration tube 27 is passed as far as an end 31. The stopper 29 can be placed in the neck of a glass receptacle 33 to form a hermetic seal. To create a partial vacuum in the receptacle 33, a tube 35 is passed through the stopper 29 with at its end a coupling 37 of the luer type generally used in the medical field, to be connected to a vacuum source (not shown in the drawing).

The outlet 25, in the description further referred to as the aspiration lumen of the aspiration tube 27, see again FIG. 5, is connected with the aspiration lumen 7 of the double lumen needle 1 via channel means that are formed by a portion of the aspiration tube 27 and a portion of the outer tube 11 and the inner tube 13 of the double lumen needle 1. A further explanation concerning this will follow later on in the description.

The aspiration lumen 7 of the inner tube of the double lumen needle and the aspiration lumen 25 of the aspiration lumen 27 are in fluid communication with each other, forming a first fluid pathway through the connector for the aspiration of an ovum. Via the tube 35 inserted into the stopper 29 of the receptacle 33 a partial vacuum can be created in the receptacle 33 whereby at the end 3 of the double lumen needle an ovum can be aspirated from a follicle and, via the aspiration lumen 7, via the fluid pathway in the connector 17 and via the aspiration tube 27, this can be transferred to the receptacle 33.

Between the two ends 21 and 23 of the connector body 19 of the connector 17 there is a flushing inlet 39 for the supply of a flushing fluid. To this end a feed tube 41 is provided for the flushing fluid, which at one end is provided with a luer type coupling 43 for connecting to a source of flushing fluid. At the outside of the connector body 19 a counter connector 45 of the luer type is provided, also referred to as a female connector, for cooperating with a further luer type coupling 47, also referred to as a male coupling, provided at the end of the feed tube 41 opposite the luer coupling 43. By coupling the luer coupling 47 to the counter coupling 45, a fluid pathway to a fluid source is created. In a manner that will be described later, the flushing inlet 39 is in fluid communication with the flushing lumen 9, to form a second fluid pathway for flushing a follicle.

Figure 6:
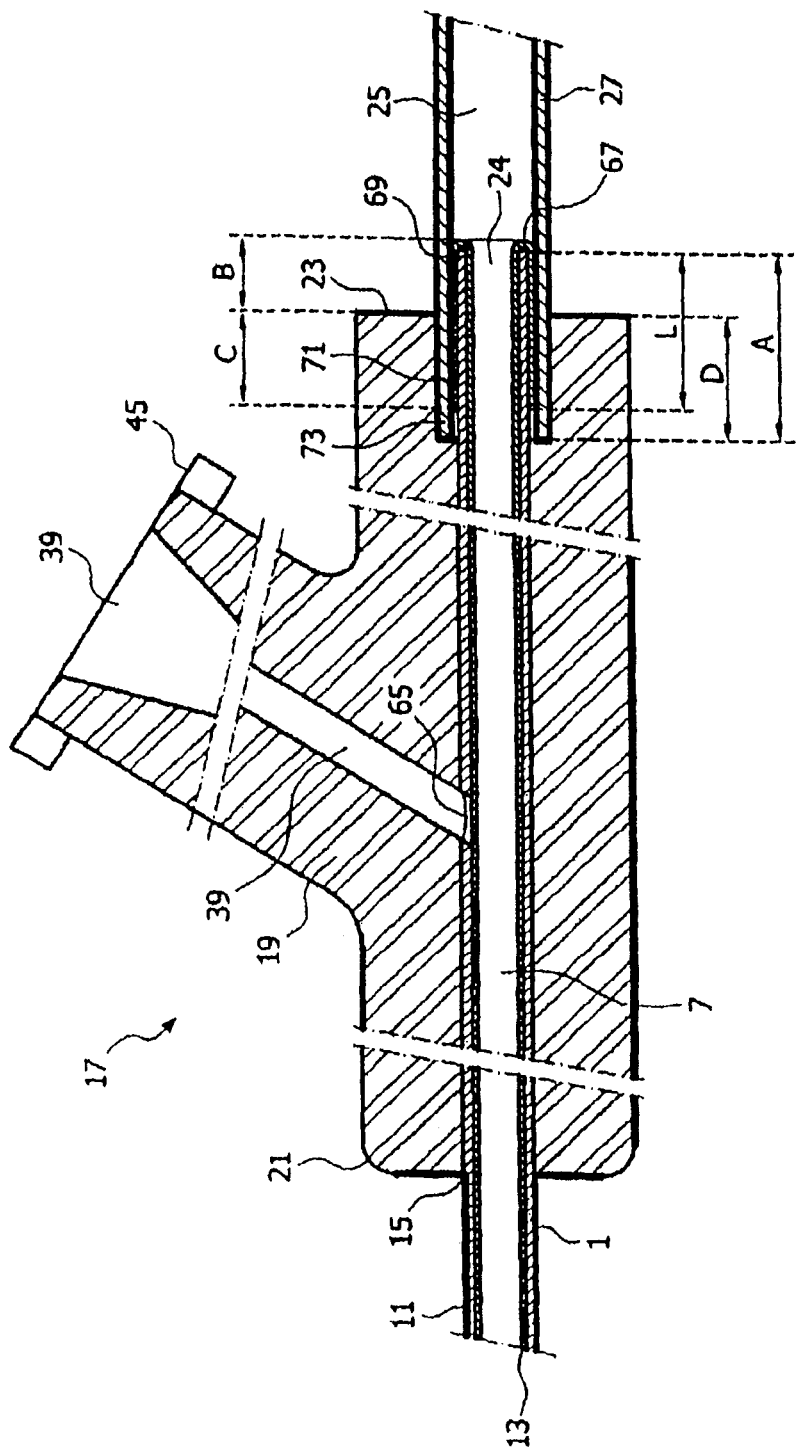
FIG. 6 shows a cross-sectional schematic side view, broken in several places, of an injection-moulded connector of an apparatus according to the invention.

As will be obvious from FIG. 6, the two liquid pathways within the connector 17 and also within the double lumen needle 1 are completely separate from each other, except near the needle end 3 of the double lumen needle.

In accordance with the invention, the lumen 7 of the inner tube 13 is the aspiration lumen. Viewed in cross section, the inner tube 13 comprises at least over part of its circumference a depressible part, which in the embodiment shown in the FIGS. 1, 2 and 3 is indicated with reference numeral 49.

This depressible part 49 is depressible as a result of a pressure difference which, during normal use of the apparatus for harvesting an ovum from a follicle, occurs between the aspiration lumen 7 and the flushing lumen 9. FIG. 2 schematically shows that the depressible part 49 extends approximately over a length of arc that corresponds to an angle α.

The depressible part 49 is shown to be elastically deformed between the shape drawn as a continuous line and the shape drawn as a broken line. It is assumed that the shape drawn as a continuous line 49 is approximately sinusoidal, with a dip between two tops. Whether this will be the shape in reality is a matter to be determined by the shape of the inner tube 13, the material chosen for the inner tube 13 and the pressure difference occurring between the flushing lumen 9 and the aspiration lumen 7.

Figure 2:
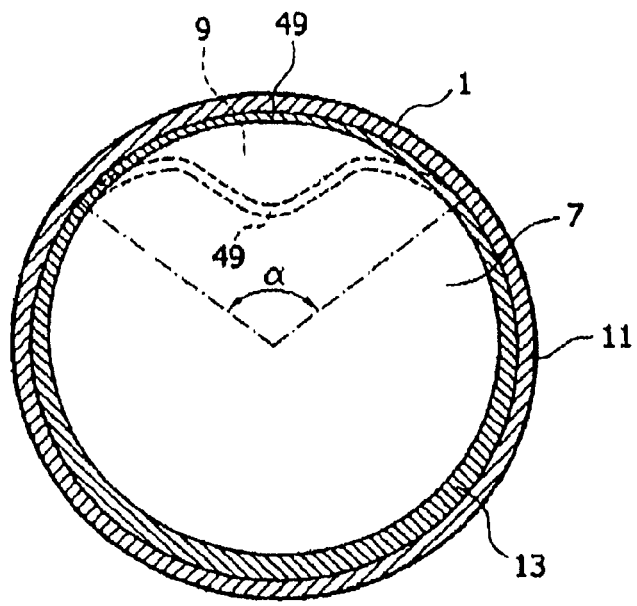
FIG. 2 shows a cross-sectional view through a double lumen needle of the apparatus according to the invention, provided with an inner tube with an eccentric aspiration lumen.

In the embodiment shown in the FIGS. 2 and 3, the outside diameter of the inner tube 13 is in the non-depressed state with the depressible part 49 drawn as continuous line, shown to be substantially the same as the inside diameter of the outer tube 11. This non-depressed state will occur, for example, in the absence of a pressure difference between the flushing lumen 9 and the aspiration lumen 7. The dimensions of the outer tube 11, the inner tube 13 and the depressible part 49 are chosen such that an ovum, possibly surrounded by some tissue, is able to pass through the aspiration lumen in the axial direction of the double lumen needle without thereby completely obstructing the flushing lumen 9. Whatever the circumstances, flushing fluid will always be able to flow from the flushing lumen 9 to the follicle.

In the FIGS. 2 and 3, an embodiment is clearly represented, showing the inner tube 13 to have a variable wall thickness with, viewed cross-sectionally, a thinner portion at the depressible part 49 that continues to become thicker at the opposite side. In essence, the inner tube is a cylindrical tube with a likewise cylindrical aspiration lumen 7 eccentrically placed therein. The entire inner tube 13 is made of a suitable elastic plastic. The person skilled in the respective art is able to use an elastic material known in the art to be suitable for medical applications.

Figure 4:
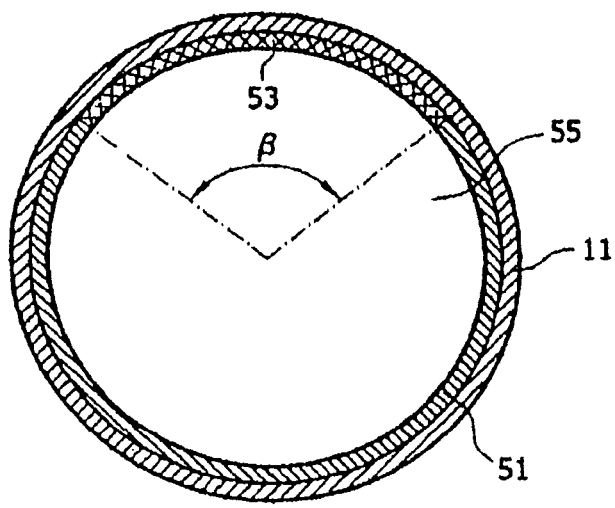
FIG. 4 shows a cross section similar to that of FIG. 2 of a different embodiment of the invention.

FIG. 4 shows an embodiment of the invention wherein an inner tube 51 of a different design is placed inside the outer tube 11 of the double lumen needle. In this embodiment, a depressible portion 53 of the inner tube 51 is made of a different material than the remaining part of the inner tube 51. The Figure shows a cylindrical tube 51 in which a concentric aspiration lumen 55 is provided and having a substantially constant wall thickness. The material of the portion 53 of the wall of the tube 51 is more flexible than that of the remaining part of the inner tube 51. The depressible part 53 is preferably characterized by a visible feature distinguishing it from the remaining part of the inner tube 51. As will become clear later, this is very useful when placing the inner tube into the outer tube, because the inner tube has to have a particular angular orientation in relation to the outer tube in order to ensure that the flushing inlet 39 inside the connector body 19 of the connector 17 opens into the flushing lumen for the supply from outside of flushing fluid.

The interior surface of the inner tube 13 or 51, respectively, of the two embodiments discussed as well as all other possible embodiments, is preferably made of a biocompatible material, inside the double lumen needle, the ovum and any possibly entrained surrounding tissue comes in contact solely with the interior wall of the inner tube which, indeed, acts as aspiration tube. It is therefore of importance that the interior surface of this tube consists of biocompatible material. Preferably the entire inner tube is made of biocompatible plastic. This dispenses with a separate biocompatible layer on the inside of the inner tube. The inner tube 51 according to the embodiment of FIG. 4 could suitably be manufactured in plastic by means of a method of coextrusion, in two different plastic materials with the material of the depressible part 53 being more elastic than that of the remaining part of the inner tube 51. Co-extrusion is a method well-known in the prior art, wherein during an extrusion process extrusion products made of two or more different materials are manufactured. These processes are well-known to the persons skilled in the art of extrusion processes.

The inner tube 13 according to the embodiment of FIG. 2 may be entirely made of elastic material and the depressible part 49 may be elastically deformable. Likewise, the inner tube 51 according to FIG. 4 may be entirely made of elastic material with the depressible part 53 being elastically deformable, due to the depressible part 53 being made of a material that is more elastic than that of the remaining part of the inner tube 51.

FIG. 5 shows still another embodiment of the invention, which has a round inner tube 57 and a concentric aspiration lumen 59. In this embodiment the inner tube 57 is entirely made of an elastic synthetic material. The depressible part 61 extending over an arc length that corresponds with the angle γ in the drawing is provided with grooves 63 running in the axial direction over the exterior wall of the inner tube 57. These grooves, which in the embodiment shown in FIG. 5 are equidistant from each other and have the same shape and depth, locally weaken the wall of the inner tube 57. This makes it easier to depress the depressible portion 61 than the remaining part of the inner tube 57. In this embodiment also the inner tube 57 is entirely made of biocompatible plastic and the depressible part 63 is visibly distinguishable from the remaining part of the inner tube.

An interesting embodiment of the invention with respect to fitting an inner tube of elastic material inside the outer tube of the double lumen needle is one whereby the inner tube consist of an elastic material that can be stretched in the axial direction when subjected to axial tensile forces, such as to simultaneously elastically reduce the outside diameter to an outside diameter that is smaller than the inside diameter of the outer tube, while, in the absence of axial tensile forces the inner tube furthermore, exerts an elastic radial pressure on the interior surface of the outer tube.

This embodiment of the invention may be very conveniently applied with the embodiments of the double lumen needle shown in the FIGS. 2 to 5. In these embodiments, the inner tubes 13, 51 and 57, respectively, may consist of elastic material that is stretchable in the axial direction with a simultaneous reduction of the outside diameter. In the situation shown in the FIGS. 2 to 5 and when applying the above-mentioned embodiment, the inner tubes 13, 51, or 57, respectively, will then be jammed under radial elastic pressure against the outer tube 11.

For this embodiment of the invention a method in accordance with the invention may be used that comprises the provision of an outer tube and the provision of an inner tube made of elastic material having an outside diameter that, when axially not stretched, is larger than the inside diameter of the outer tube. Subjecting the opposite ends of the inner tube to opposing axial forces causes the same to be axially stretched, simultaneously radially reducing the outside diameter to a stretched condition where the reduced outside diameter of the inner tube is smaller than the inside diameter of the outer tube. In this stretched condition the inner tube is fitted into the outer tube after which the above-mentioned axial forces are cancelled allowing the inner tube to expand radially, such that due to an elastic radial pressure exerted on the interior wall of the outer tube, the inner tube is radially jammed inside the outer tube.

This is a quick and simple manner for fitting the inner tube inside the outer tube, for example, with the aid of a draw wire or tie rod. It is not necessary for the inner tube to fit precisely inside the outer tube, since the inner tube is elastic and will expand radially so as to jam it against the interior wall of the outer tube.

Prior to this, the inner tube may be made to length. If, after fitting, the inner tube projects from the outer tube, it may be shortened.

FIG. 6 schematically shows a cross section of the connector 17 of the apparatus according to FIG. 1. This connector is injection-moulded around the outer tube 11 in the known manner. Inside the connector 17, the outer tube 11 is provided with a through opening 65 in the wall near the flushing lumen 9 and, while being outwardly hermetically sealed, is in fluid communication with a flushing inlet extending to the outside of the connector 17, for the supply of flushing fluid. The inner tube 13 consists of elastic material and is at the proximal end 61 elastically folded back over a particular foldback length L over the outside of the distal end 69 of the outer tube 11. Covering a particular length A at the outside, a distal end 73 of the flexible aspiration tube 27 having an aspiration lumen 25 is provided over the fold-back portion 71 of the inner tube 13. In this way at least part of the fold-back portion 71 of the inner tube 13 is located at said application length A between the exterior wall of the proximal end 69 of the outer tube 11 and the interior wall of the distal end 73 of the flexible aspiration tube 27. In the embodiment of FIG. 6, the application length A is even greater than the foldback length L, so that the distal end 73 of the aspiration tube 27 extends beyond the foldback portion 71 of the inner tube 13 of the double lumen needle 1.

The proximal end 69 of the outer tube 11 extends over an axial portion B, which is shorter than said folded back length L of the foldback portion 71 of the inner tube 13, to beyond the connector 17. Thus a portion C of the foldback portion 71 is inside the connector 17. The distal end 73 of the flexible aspiration tube 27 is thus provided over an injected portion D, inside the connector 17, where it provides an outwardly hermetically sealed fluid communication between the aspiration lumen 7 of the inner tube 13 and the aspiration lumen 25 of the flexible aspiration tube 27.

To manufacture the apparatus shown, a method may be used in accordance with the invention wherein a flexible aspiration tube 27 is provided that has an aspiration lumen 25 for connecting to the double lumen needle 1. A portion 71 of the inner tube 13 made of elastic material is at the proximal end 67 folded back over a length L to the outside of the proximal end of the outer tube 11. As an aid, a conical object may be inserted into the lumen 7 of the elastic tube 13 at the proximal end 67, in order to stretch it slightly. Using, for example, a rubber glove, the inner tube 13 may subsequently be folded back over the external surface of the outer tube 11.

At the outside of the foldback portion 71 of the inner tube 13 a distal end 73 of a flexible aspiration tube 27 is provided over a particular application length A, such that at least a part of the foldback portion L of the inner tube 13 is positioned at the said application length A between the exterior wall of the proximal end of the outer tube 11 and the interior wall of the distal end 73 of the flexible aspiration tube 27.

As mentioned before, in the embodiment of the drawing the application length A is even slightly greater than the folded back length L. The proximal end 69 of the outer tube 11, the foldback portion 71 of the inner tube 13 and the distal end 73 of the flexible aspiration tube 27 are now placed into an injection mould, not shown in the drawing, having a mould cavity for shaping the connector 17 by injection moulding.

The proximal end of the outer tube 11 then extends over an axial portion B that is shorter than said folded back length L of the foldback portion 71 of the inner tube 13 to beyond the mould cavity, such that a portion C of said folded back length L of the inner tube 13 is inside the mould cavity. In this situation liquid plastic is injected into the mould cavity. After the injected plastic is cured, the connector is removed from the mould cavity. The distal end 73 of the flexible aspiration tube 27 is then positioned over an injected portion D located inside the connector 17 and locally provides an outwardly hermetically sealed fluid connection between the aspiration lumen 7 of the inner tube 13 and the aspiration lumen 25 of the flexible aspiration tube 27.

With this method it is extremely important that during the injection of plastic into the mould cavity of the injection mould the distal portion 73 of the aspiration tube 27 is internally supported by the proximal portion of the double lumen needle 1 formed by the proximal portion 69 of the outer tube and the foldback portion 71 of the inner tube. Otherwise, the injection pressure generated during injection of the liquid plastic would crush the flexible aspiration tube 27.

The outlined method provides a quick and economical manner of realising a fluid proof connection between the double lumen needle 1 and the aspiration tube 27 in such a manner that a fluid communication is created between the aspiration lumen 7 of the inner tube 13 of the double lumen needle and the aspiration lumen 25 of the aspiration tube 27.

The method discussed may also be arranged such that in a quick and simple manner during injection the flushing inlet 39 is formed at the same time for the supply of flushing fluid to the flushing lumen 9 inside the double lumen needle. As is clearly visible from FIG. 6, the connection between the flexible aspiration tube 27 and the double lumen needle 1 is such that at the proximal end of the double lumen needle no flushing liquid can leak from the flushing lumen to the aspiration lumen 25 of the aspiration tube 27, or to the aspiration lumen 7 of the inner tube 13.

The method comprises the provision of a through opening 65 in the wall of the outer tube 11, located some distance from the proximal end 69 of the outer tube 11 of the double lumen needle and inside the connector 17 to be formed. When the double lumen needle 1 and the aspiration tube 27 provided thereon are positioned in the mould cavity, an axially movable pin (not shown in the drawing) that is to be placed against the outer tube and that forms a seal to liquid plastic, is inserted into the mould cavity at the through opening 65 in the outer tube 11 of the double lumen needle.

After curing the injected plastic and after withdrawal of said pin, a flushing inlet 39 having the diameter of the axially withdrawn pin is formed in the flushing body 19, thereby forming a feed channel for flushing fluid from the outside of the connector, via the flushing inlet 29 and the through opening 65 through the outer tube 11 to the flushing lumen 9 of the double lumen needle 1. Movable pins that can be slid in and out of a mould cavity of an injection mould axe well-known in the art and the person skilled in the art is well able to apply them.

While the invention is explained by way of some exemplary embodiments, they do not limit the invention in any way. On the contrary, the invention comprises every possible embodiment of an apparatus falling within the frame of the description given in claim 1. It will be obvious to those skilled in the respective field of technology that numerous modifications and variations are possible within the scope of the invention. For example, the materials used may be chosen in concurrence with the developing medical insights and the developing technology in the field of materials. The depressible part of the inner tube may, for example, be of a different nature than the elastically deformable depressible parts shown in the drawing and discussed above. For example the depressible part may, at least locally, be relatively stiff and be depressible by bending or folding over in certain places. In the absence of a pressure difference between the interior wall of the outer tube and the exterior wall of the inner tube, the inner tube does not need to be in contact over its entire circumference. The inner tube may be attached to the outer tube by local adhesion, fusion or welding.

What is claimed is:

1. An apparatus for transferring an ovum from a follicle with a technique of simultaneous flushing and aspiration, which apparatus comprises:
 a double lumen needle having at the distal needle end to be inserted into the follicle an aspiration lumen for removing an ovum from a follicle and a flushing lumen for inserting a flushing fluid into the follicle,
 the double lumen needle comprising an outer tube with an internally located inner tube that extends over at least part of the length of the outer tube,
 one of the lumens being bounded by the inner surface of the inner tube and the other of the two lumens by the space between the outer surface of the inner tube and the inner surface of the outer tube, and a connector having a connector body which at a first distal connector end is connected to the proximal needle end remote from the distal needle end, having an outlet at a second connector end for discharging the flushing fluid with possibly an ovum to an exterior and having a channel means that connects the outlet with the aspiration lumen and defines a first fluid pathway for aspirating an ovum and having a flushing inlet between the two ends of the connector body for supplying the flushing fluid and, in fluid communication with the flushing lumen, for defining a second fluid pathway for flushing a follicle, wherein the two fluid pathways within the connector and the double lumen needle are separated from each other, and wherein the inner tube comprises a deformable material, and wherein:

the lumen of the inner tube is the aspiration lumen of the double lumen needle, viewed in cross section, the inner tube comprises at least over part of its circumference a depressible part that is depressible as a result of a pressure difference which occurs during normal use between the aspiration lumen and the flushing lumen, and wherein the flushing lumen, at least during flushing, consists of a space between the inner surface of the outer tube and the outer surface of said depressible part of the inner tube, and wherein the inner tube exerts an elastic radial pressure on the inner surface of the outer tube, thereby attaching itself to the outer tube, and wherein the entire inner tube is made of elastic material and the depressible part is elastically deformable, and wherein the inner tube consists of a material that can be elastically stretched in the axial direction such as to simultaneously elastically reduce the outside diameter to a reduced outside diameter that is smaller than the inside diameter of the outer tube, and the inner tube, exerts an elastic radial pressure on the interior surface of the outer tube.

2. An apparatus according to claim 1, wherein the outside diameter of the inner tube in the non-depressed state is substantially the same as the inside diameter of the outer tube.

3. An apparatus according to claim1, wherein the inner tube has a variable wall thickness where, viewed cross sectionally, a thicker portion is followed by a thinner portion, with said depressible part being provided at the thinner portion.

4. An apparatus according to claim 1, wherein the depressible part of the inner tube is manufactured in a different material than the remaining part of the inner tube.

5. An apparatus according to claim 1, wherein that the inner tube has an inner surface that is made of a biocompatible material.

6. An apparatus according to claim 5, wherein the entire inner tube is made of a biocompatible plastic.

7. An apparatus according to claim 1, wherein the inner tube is manufactured by means of coextrusion, in two different plastic materials.

8. An apparatus according to claim 1, wherein the depressible part is visibly distinguishable from the remaining part of the inner tube.

9. A method for the manufacture of an apparatus in accordance with claim 1, wherein the method comprises the steps of:

providing an outer tube, providing an inner tube made of elastic material, whose outside diameter in the axially non-depressed state is larger than the inside diameter of the outer tube, applying opposing axial forces to the opposite ends of the inner tube to axially stretch the inner tube, causing the simultaneous radial reduction of the outside diameter to a stretched condition where the reduced outside diameter of the inner tube is smaller than the inside diameter of the outer tube, and in said stretched condition fitting the inner tube into the outer tube and cancelling said axial forces, allowing the simultaneous radial expansion of the inner tube and causing the inner tube to radially jam inside the outer tube, and wherein the inner tube exerts an elastic radial pressure on the inner surface of the outer tube, thereby attaching itself to the outer tube.

10. An apparatus according to claim 1, wherein the connector is provided around the outer tube by injection moulding, the outer tube is provided inside the connector with a through opening in the wall near the flushing lumen and, while being outwardly hermetically sealed, is in fluid communication with a flushing inlet extending to the outside of the connector.

11. An apparatus according to claim 10, wherein the inner tube consist of elastic material and is at the distal end elastically folded back over a particular foldback length L, over the foldback portion of the inner tube at its outside over a particular application length (A), a distal end of a flexible aspiration tube having an aspiration lumen is provided, such that at least part of the foldback portion of the inner tube is located at said application length (A) between the exterior wall of the proximal end of the outer tube and the interior wall of the distal end of the flexible aspiration tube, the proximal end of the outer tube extends over an axial portion (B), which is shorter than said folded back length (L) of the foldback portion of the inner tube to beyond the connector, such that a portion (C) of the foldback portion is inside the connector, and the distal end of the flexible aspiration tube is provided over an injected portion (D) inside the connector, where it provides an outwardly hermetically sealed fluid connection between the aspiration lumen of the inner tube and the aspiration lumen of the flexible aspiration tube.

12. A method for the manufacture of the apparatus in accordance with claim 11, wherein the method comprises the steps of:

providing a flexible aspiration tube having an aspiration lumen for connecting to a double lumen needle of the apparatus according to the invention, at its proximal end elastically folding back a portion of the inner tube made of elastic material over a certain folded back length (L), providing over the foldback portion of the inner tube at its outside over a particular application length (A) a distal end of a flexible aspiration tube having an aspiration lumen, such that at least part of the foldback portion (L) of the inner tube is located at said application length (A) between the exterior wall of the proximal end of the outer tube and the interior wall of the distal end of the flexible aspiration tube, placing the proximal end of the outer tube, the proximal end of the inner tube and the distal end of the flexible aspiration tube into an injection mould having a mould cavity for forming the connector by injection moulding, wherein the proximal end of the outer tube extends over an axial portion (B) that is shorter than said folded back length (L) of the foldback portion of the inner tube to beyond the mould cavity, such that a portion (C) of said folded back length (L) of the inner tube is inside the mould cavity, and injecting liquid plastic into the mould cavity, and after curing the injected plastic, removing the apparatus with the injected connector from the mould cavity, such that the distal end of the flexible aspiration tube is positioned over an injected portion (D) inside the connector providing an outwardly hermetically sealed fluid connection between the aspiration lumen of the inner tube and the aspiration lumen of the flexible aspiration tube.

13. The method of claim 12, wherein the method additionally comprises the steps of:

providing a through opening in the wall of the outer tube, located some distance from the proximal end of the double lumen needle and inside the connector to be formed, placing an axially movable pin against the outer tube into the mould cavity at the through opening so as to substantially form a seal to liquid plastic, and after curing the injected plastic, axially withdrawing said pin, whereby from the outside of the connector a flushing inlet is formed which, via the through opening through the outer tube, is in fluid communication with the flushing lumen of the apparatus.

* * * * *